US010189044B2

United States Patent
Forsythe et al.

(10) Patent No.: US 10,189,044 B2
(45) Date of Patent: Jan. 29, 2019

(54) APPARATUS AND SYSTEMS FOR APPLYING A LIQUID CROP-PRESERVATIVE FORMULATION TO A CONTAINER

(71) Applicant: 1,4 Group, Inc., Meridian, ID (US)

(72) Inventors: John M. Forsythe, Nampa, ID (US); Curtis Lee Eames, Meridian, ID (US); Jan W. de Weerd, Meridian, ID (US); James Zalewski, Boise, ID (US)

(73) Assignee: 1,4 Group, Inc., Meridian, ID (US)

( * ) Notice: Subject to any disclaimer, the term of this patent is extended or adjusted under 35 U.S.C. 154(b) by 0 days.

(21) Appl. No.: 15/214,183

(22) Filed: Jul. 19, 2016

(65) Prior Publication Data

US 2016/0325298 A1    Nov. 10, 2016

Related U.S. Application Data

(62) Division of application No. 13/743,258, filed on Jan. 16, 2013, now Pat. No. 9,392,805.

(51) Int. Cl.

| | | |
|---|---|---|
| *B05B 13/02* | (2006.01) | |
| *A23B 7/144* | (2006.01) | |
| *A23B 7/158* | (2006.01) | |
| *A23B 7/16* | (2006.01) | |
| *A01N 25/02* | (2006.01) | |

(Continued)

(52) U.S. Cl.
CPC .......... *B05B 13/0221* (2013.01); *A01N 25/02* (2013.01); *A23B 7/144* (2013.01); *A23B 7/158* (2013.01); *A23B 7/16* (2013.01); *A23L 3/34* (2013.01); *B05D 7/227* (2013.01); *A23V 2002/00* (2013.01)

(58) Field of Classification Search
None
See application file for complete search history.

(56) References Cited

U.S. PATENT DOCUMENTS

| | | |
|---|---|---|
| 3,008,839 A | 11/1961 | Louis et al. |
| 4,168,662 A | 9/1979 | Fell et al. |

(Continued)

FOREIGN PATENT DOCUMENTS

| | | |
|---|---|---|
| WO | 9302563 A1 | 2/1993 |
| WO | 9509535 A2 | 4/1995 |
| WO | 2012031174 A2 | 3/2012 |

OTHER PUBLICATIONS

Campbell et al., "The sprout inhibitor 1,4-dimethylnaphthalene induces the expression of the cell cycle inhibitors KRP1 and KRP2 in potatoes," Functional & Integrative Genomics, vol. 12, No. 3, (2011), pp. 533-541.

(Continued)

*Primary Examiner* — Jethro M. Pence
(74) *Attorney, Agent, or Firm* — Magleby Cataxinos & Greenwood

(57) ABSTRACT

A method for treating a substrate with a volatile liquid, crop-preservative formulation includes transporting a predetermined quantity of the formulation from a reservoir to an injection device and applying the predetermined quantity to the substrate. The substrate may thereafter be in proximity to a crop to be treated by the vapor from the formulation. The substrate is most conveniently a portion of a container in which the crop is stored or shipped.

6 Claims, 3 Drawing Sheets

(51) Int. Cl.
*A23L 3/34* (2006.01)
*B05D 7/22* (2006.01)

(56) References Cited

U.S. PATENT DOCUMENTS

| | | | |
|---|---|---|---|
| 4,860,490 A * | 8/1989 | Morris | A01G 31/02 47/59 R |
| 5,129,951 A | 7/1992 | Vaughn | |
| 5,139,562 A | 8/1992 | Vaughn et al. | |
| 5,334,619 A | 8/1994 | Vaughn et al. | |
| 5,580,596 A | 12/1996 | Winkelmann et al. | |
| 5,622,912 A | 4/1997 | Riggle et al. | |
| 5,849,678 A | 12/1998 | Murch et al. | |
| 5,918,537 A | 7/1999 | Forsythe et al. | |
| 5,935,660 A | 8/1999 | Forsythe et al. | |
| 5,957,044 A | 9/1999 | Kravitz | |
| 6,010,728 A | 1/2000 | Forsythe et al. | |
| 6,068,888 A | 5/2000 | Forsythe et al. | |
| 6,313,073 B1 | 11/2001 | Farooqi et al. | |
| 6,338,296 B1 | 1/2002 | Forsythe et al. | |
| 6,367,488 B1 | 4/2002 | Murch et al. | |
| 6,375,999 B1 | 4/2002 | Forsythe et al. | |
| 6,403,536 B1 | 6/2002 | Forsythe et al. | |
| 6,432,882 B1 | 8/2002 | Yamamoto | |
| 6,541,054 B2 | 4/2003 | Forsythe et al. | |
| 6,855,669 B2 | 2/2005 | Knowles et al. | |
| 7,393,400 B2 | 7/2008 | Kitawaki et al. | |
| 8,329,618 B1 | 12/2012 | Schafer et al. | |
| 9,392,805 B2 | 7/2016 | Forsythe et al. | |
| 2006/0097010 A1 * | 5/2006 | Riney | B05C 5/001 222/146.5 |
| 2007/0290062 A1 | 12/2007 | Forsythe et al. | |
| 2008/0223227 A1 | 9/2008 | Robbs et al. | |
| 2012/0258859 A1 | 10/2012 | Knowles et al. | |
| 2014/0199450 A1 | 7/2014 | Zalewski et al. | |
| 2014/0199465 A1 | 7/2014 | Forsythe et al. | |

OTHER PUBLICATIONS

International Search Report and Written Opinion for PCT/US2013/021761, dated Oct. 11, 2013, 12 pages.

* cited by examiner

APPARATUS AND SYSTEMS FOR APPLYING A LIQUID CROP-PRESERVATIVE FORMULATION TO A CONTAINER

CROSS-REFERENCE TO RELATED APPLICATIONS

This application is a divisional of U.S. patent application Ser. No. 13/743,258, filed Jan. 16, 2013, and is also related to U.S. patent application Ser. No. 13/743,236, filed Jan. 16, 2013, now abandoned, the disclosure of each of which is hereby incorporated in its entirety herein by this reference.

TECHNICAL FIELD

This invention generally relates to a process and apparatus for indirectly treating crops with vapors from a volatile liquid crop preservative. Particular embodiments also relate to apparatus and methods for treating potatoes after storage to prevent sprouting during shipment to warehouses, grocery stores, and the like, especially in small containers such as cardboard boxes, bags, and the like.

BACKGROUND

Tubers, especially potatoes, are treated with sprout inhibitors during storage (see, U.S. Pat. No. 6,010,728). These techniques involve placing, upon the potato, a residue of a sprout inhibitor, especially CIPC. Currently, potatoes removed from storage are treated directly with a sprout inhibitor, such as a water-based formulation of CIPC (chloroisopropyl carbamate). Alternatively, aerosol containers filled with DMN (dimethylnaphthalene) are placed in trucks to provide an enveloping vapor of DMN during shipment to a store or other destination.

These techniques have shortcomings. Many consumers do not want ware potatoes (potatoes to be consumed as such) to contain CIPC, a synthetic chemical that has EPA restrictions relating to residues on potatoes. The DMN vapor technique from aerosol containers is effective, but some truck operators forget to install them in the enclosed truck box. Often, these potatoes are placed in cardboard boxes, which are packed tightly in the truck, minimizing circulation of DMN vapor from an aerosol container. Patents relating to release of DMN vapors include U.S. Pat. Nos. 6,541,054, 5,918,537, 6,338,296, and 6,403,536.

BRIEF SUMMARY

The instant invention relates to apparatus and methods for treating small containers, such as cardboard boxes, paper bags, and the like, with a predetermined quantity of a volatile crop preservative chemical. Use of a volatile chemical such as DMN, especially 1,4-DMN, results in its subsequent volatilization to provide a contained-vapor of DMN, for example, within the cardboard box or other suitable container.

The apparatus and methods are structured to apply a small, predetermined quantity of volatile liquid chemical (e.g., DMN) onto an interior surface of a box or any other suitable container. The technique generally involves injecting a predetermined quantity of volatile crop-preservative chemical onto the interior surface of a cardboard box, paper bag, or similar small container just prior to that box or other container being filled with clean crops (e.g., ware potatoes or other crops such as berries, onions and the like) prior to shipment to market.

Generally, it is desired that any surface containing a deposit of liquid volatile chemical be positioned so that it doesn't contact the surface of a crop (e.g., potato) to prevent surface damage to such a crop. Only the vapors from a deposited predetermined quantity of liquid volatile chemical (e.g., DMN) are intended to reach the potatoes. This vapor generation is generated when the liquid volatile chemical is applied directly to an interior of a box or other container.

In a particular embodiment, the instant apparatus and process can be integrated with the continuous or semi-continuous system for filling containers with potatoes. A filling station may place various quantities of potatoes in a container; for example, the potato-dispensing machine may dispense 5 lb, 20 lb, or 25 lb of potatoes at various periods of time. A feedback loop from the potato-dispensing machine to the chemical injection apparatus then controls the appropriate quantity, especially the proper amount of active ingredient to be applied to a box or carton for a particular weight of potatoes.

DETAILED DESCRIPTION

Figure 1:
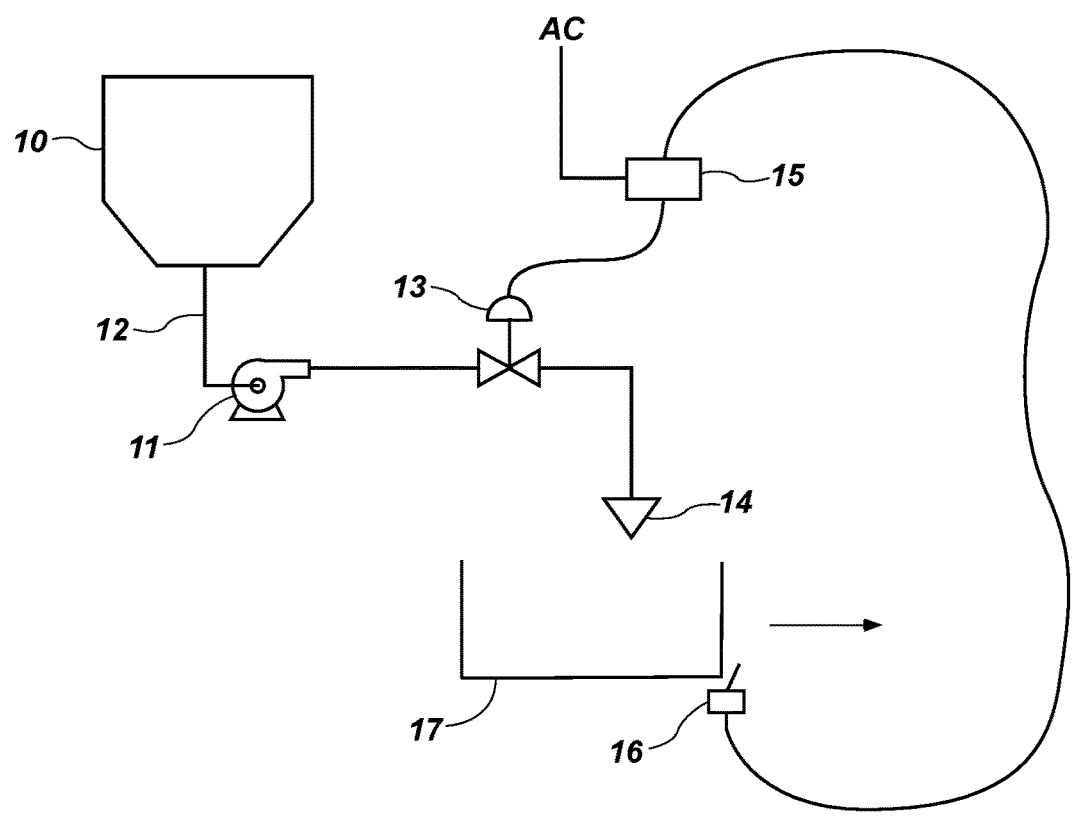
FIG. 1 is a block diagram illustrating one embodiment of the invention.

A particular embodiment of the disclosure is made with reference to FIG. 1, which illustrates an apparatus and method for applying a predetermined quantity of liquid DMN to the interior surface of a box. The crop to be treated, in one example, is potatoes, in order to preclude or minimize sprouting, dehydration, and/or loss of turgidity during shipment to market.

Potatoes for shipment to stores (ware potatoes) are generally placed in boxes at a filling station as the boxes are conveyed along a conveyor in a substantially continuous manner. In FIG. 1, such an empty box 17 is shown at a first position. A sensor or trigger 16 senses the position of an empty box and sends a signal to controller 15, which sends an actuator signal to a solenoid valve 13. Solenoid valve 13 can be a metering valve and can be opened for a controlled period of time to cause an injection of a predetermined, small quantity of DMN or other volatile sprout inhibitor to be injected into box 17 from an injection nozzle 14. Injection nozzle 14 may be structured to squirt a tight stream or a fan-like spray of liquid chemical, depending upon the particular deposit of chemical desired on the box surface. If the box surface is absorbent, a tight stream of liquid may be applied to penetrate into the absorbent surface to provide for a time-release effect of the vapor. If the box surface is more dense (i.e., less absorbent) a larger imprint of chemical onto the surface may be applied.

The liquid chemical can be stored in a container 10 to flow, by gravity, through line 12 to pump 11, which provides a pressurized stream of liquid chemical to solenoid valve 13. A constant pressure of chemical liquid may be used so that a predetermined amount of liquid chemical will be injected through solenoid valve 13 when it is opened for a predetermined period of time. Controller 15 may be pre-set to control the amount of time solenoid valve 13 is open, thereby controlling the quantity of liquid chemical, which is ejected from nozzle 14. A needle-type valve may be used to control the quantity of liquid ejected.

Pump 11 could be omitted if tank 10 were to be placed at a very elevated position above solenoid valve 13, so that gravity (pressure head of liquid) would provide a sufficient constant pressure of liquid chemical to solenoid valve 13. In order to have a predetermined quantity of liquid chemical ejected from nozzle 14, a constant liquid pressure may be effected on solenoid valve 13.

The quantity of liquid chemical to be injected into the box 17 depends upon the type of chemical, its efficacy as a crop preservative, the concentration of active ingredient in the liquid chemical, the quantity and type of crops to be placed in the box, the condition of the crop, and estimated transit time of the box to the ultimate destination of the crop (e.g., a grocery store).

The filling process may include empty boxes being transported on a conveyor in a continuous manner or, alternatively, in intermittent movement. In the embodiment of FIG. 1, box 17 is shown in a first position where a predetermined quantity of liquid chemical is injected into the box. The box is then conveyed to a filling station where a predetermined quantity (weight) of potatoes is dropped into the box. The potatoes may be loose or bagged, in plastic or paper bags, which can contain ventilation pores therein so the potatoes may respire and the chemical vapors can intrude into the bag interior, surround the potatoes, and then be absorbed thereon. The boxes then proceed to another station where the boxes are sealed.

The liquid chemical utilized may be a DMN, such as 1,4-DMN, or a formulation that contains a diluent, a solvent, surfactant or other additive to achieve a particular purpose. 1,4-DMN is marketed as 1,4SIGHT® and may be obtained from 1,4 Group, Meridian, Id. Other additions may include aroma enhancers, deodorizers, essential oils, higher alcohols of
$C_6$-$C_{12}$ carbon length, and the like.

DMN was shown to be effective on sprouting root and tuber crops including, but not limited to, beet, carrot, cassava, dasheen (taro), ginger, ginseng, horseradish, parsnip, potato, sweet potato, turnip, and yam. DMN was also shown to be effective on sprouting bulb crops including, but not limited to, garlic, leek, onion, and shallot. DMN was also shown to be effective on sprouting ornamentals, such as flowering bulbs.

A diluent or solvent may be included in the liquid chemical for a variety of purposes. Some active ingredients, such as DMN, are expensive and a precise quantity is desired to be applied to the interior surface of the box. That quantity, for small boxes, may be so small that the solenoid valve may be open for such a small fraction of a second that precise control of liquid ejected is difficult. Thus, a diluted active ingredient in a liquid composition provides for a greater liquid quantity to be ejected and, thereby, enabling a more precise control of the quantity of active ingredient (a.i.) to be applied.

Also, a chemical composition containing a diluent may be used to effectuate a large spray pattern onto the box surface so that the evaporation rate of the active ingredient may be enhanced, if so desired. Also, other volatile active ingredients may be included in the liquid chemical composition, such as bactericides, fungicides, etc. The inclusion of surfactants to reduce surface tension and/or viscosity of the injectable liquid may be also desirably included in an injectable chemical composition.

Other volatile active ingredients, such as peppermint oil, clove oil, and other known volatile sprout inhibitors, may be included. These essential aromatic oils are, generally, sufficiently volatile to be useful. Other suitable volatile chemicals include aliphatic alcohols, especially those of a molecular size $C_6$-$C_{12}$ carbon atom. Aliphatic aldehydes and ketones may also be used, including those disclosed in Knowles, U.S. Pat. No. 6,855,669. Useful essential oils are also described in to Vaughn (U.S. Pat. Nos. 5,139,562 and 5,129,951), as well as U.S. Pat. No. 5,580,596 to Winkelman, and U.S. Pat. No. 6,313,073 to Farooqi. Also, U.S. Pat. No. 5,334,619 to Vaughn discloses 2-nonanone as a useful fungicide for treatment of berries.

These chemicals typically have a volatility in about the same range as 1,4-DMN and may be utilized in conjunction with 1,4-DMN, either as a compatible mixture or in sequence with 1,4-DMN. The above-identified chemicals may also be used separately from 1,4-DMN, either as separate active ingredients or in admixtures of such chemicals. There are volatile aromatic chemicals such as pyrazines, which have been identified as emanating from baked potatoes, which may impart a favorable baked potato aroma. A minor amount of these compounds could be included for favorable aroma purposes, without any adverse effect upon the sprout inhibiting effect of DMN. Formulations disclosed in U.S. patent application Ser. No. 13/743,236, entitled "INJECTABLE LOW TEMPERATURE LIQUID CROP PRESERVATIVE FORMULATION," filed Jan. 16, 2013, by common inventors and commonly assigned, are especially useful in the instant invention.

U.S. Pat. No. 6,403,526 disclosed certain deodorant chemicals for inclusion with DMN to mask any residual DMN odor. These chemicals may be included in the applied liquid chemical formulation utilized in the instant disclosure. The contents of that patent are incorporated herein by reference.

The quantity of active ingredient applied to a box or other small container will be dependent upon the quantity (weight) of potatoes to be placed in the box. Typical concentrations of DMN, e.g., range from about 0.5 mg per kilogram of potatoes to about 20 mg/kg. Thus, for a box holding 25 lb (approximately 12 kg), about 6.0 to about 250 mg of DMN would preferably be applied to such a container.

In FIG. 1, the quantity of liquid chemical injected into a box is determined by the orifice opening in the valve, the liquid pressure, and time period for which the valve is open upon receiving an electrical signal (power input) of the desired duration. These factors can be calculated and modified to give a certain predetermined quantity of liquid formulation per unit of time that the solenoid valve is open.

Figure 2:
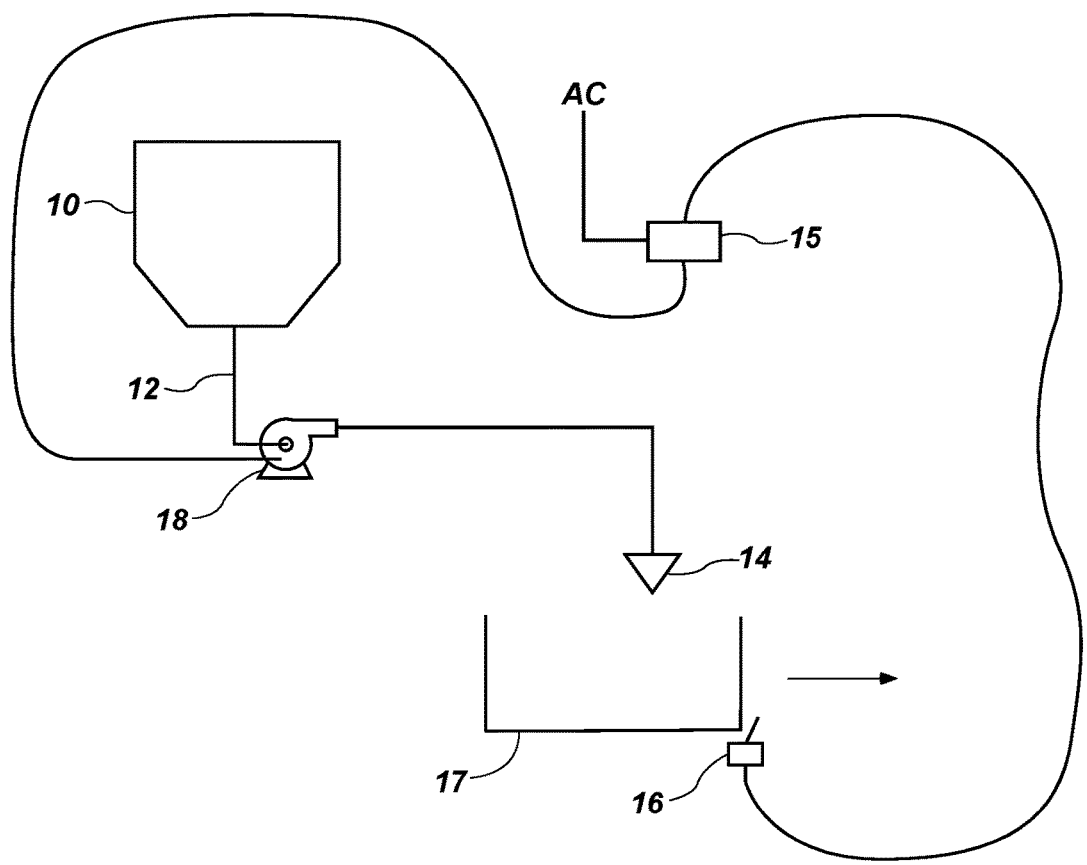
FIG. 2 is a block diagram illustrating the use of a metering pump according to another embodiment of the invention.

Another embodiment of the invention is illustrated in FIG. 2, wherein a micro metering pump 18, e.g., a very small positive displacement (piston) pump, is utilized. Such a pump will displace the contents of its cylinder on a volume per stroke of its piston. Given the minute quantities of chemical liquid to be injected, the cylinder volume of such a pump can be adjusted to be small (e.g., 0.05 ml). Multiple strokes of the piston can be used to provide for increased volumes of liquid chemical to be ejected into a box. Again, use of a diluent to reduce the concentration of active ingredients may permit use of micropumps with larger displacement.

A controller 15 controls, by the duration of an electrical signal sent to the pump that indicates the number of times the piston reciprocates, the volume of liquid chemical introduced via injection nozzle 14 into a box, bag or other container with a receptive surface.

Figure 3:
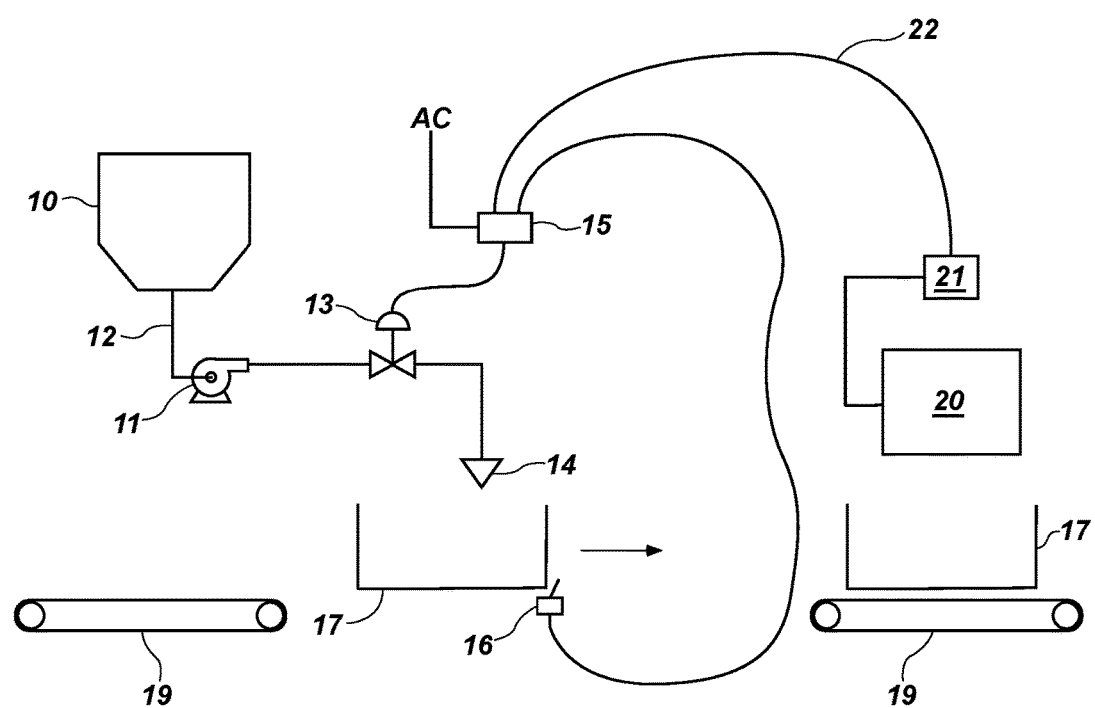
FIG. 3 is a block diagram illustrating the use of a metering pump including a feedback loop and a filling station controller according to an embodiment of the invention.

The system of FIG. 2 is similar to that of FIG. 1, except that the control liquid ejected is via a metering pump 18. A feedback loop 22 from the filling station controller 21 is shown in FIG. 3. A control function associated with the dispensing unit 20, which dispenses a controlled quantity of potatoes to be discharged from a bin into an awaiting pre-treated box 17, may send a signal via the feedback loop 22 to the liquid chemical controller to control the quantity of chemical injected into an awaiting empty box 17 sitting upon a continuous or semi-continuous conveyor 19.

Alternatively, a feedback loop may be associated with a weighing mechanism to send a signal to a liquid chemical control to account for a quantity (weight) of potatoes being placed in the box so that the proper quantity of chemical can be injected into a box. Further, the quantity of potatoes discharged into a box and the quantity of chemical ejected may be controlled manually to apply the proper quantities.

Many volatile liquid sprout inhibiting chemicals useful in the instant invention are solvents. For example, a mixture of different DMN isomers, which has been sold by Koch Chemical as a solvent, may be useful. Generally, pure 1,4-DMN, which is available from the 1,4 Group, Meridian, Id., has been the preferred DMN sprout inhibitor/dormancy enhancer used in the potato industry. It has been approved by the EPA.

Given that 1,4-DMN has solvent characteristics, a very minor quantity of a lubricant in any liquid chemical composition may be included, especially if a metering pump is used for injecting controlled quantities of DMN into a container. Suitable lubricants may include vegetable oils, mineral oils and similar food-grade lubricants, including essential aromatic oils.

Alcohols of various types, e.g., methanol, ethanol, isopropanol, are also solvents that have been used with respect to potato treatment chemical compositions. Thus, the use of these alcohols as solvents or diluents may be included alone or with a small quantity of a lubricant.

Although, "tags" may be treated with an appropriate amount of a liquid chemical composition sprout inhibitor or dormancy enhancer, as indicated in certain patents referenced above, it is very advantageous to treat the potato container since such container is large and is less likely to accidentally become part of a food made from potatoes or otherwise accidentally ingested. Also, the instant disclosure forms part of the continuous process of filling boxes with potatoes or other crops or produce to be shipped to market.

An especially desirable feature of 1,4-DMN as an injectable chemical for the purposes of this disclosure is that it diminishes sprouting of potatoes during shipment by dormancy enhancement. This type of action, in contrast to the anti-sprouting effect of CIPC, helps to preserve moisture content in the potatoes, thus providing a firm, turgid healthy-looking potato to ultimate consumers. Further, it is advantageous that 1,4-DMN is present in freshly harvested potatoes and is, thus, a naturally occurring ingredient.

The speed at which boxes are moved along a conveyor to a filling station is quite rapid. The liquid chemical injection systems described and claimed herein are suitable for rapid operation. The ability of a solenoid valve to eject a predetermined amount of liquid chemical can occur in fractions of a second. This is also true for a micro-metering pump. Thus, a liquid chemical ejection system of the present system can be implemented in a continuously conveyed, container-type filling system for potatoes.

The invention may be adjusted on-site via the controller to regulate the quantity of chemical injected into a container in a continuous or semi-continuous conveyor system. Also, the controller can control the period (time lapse) between injections. Thus, the system can be integrated with the filling system for filling boxes with potatoes, such as ware potatoes.

The system and method of the instant invention has been described as being useful in treating containers to be filled with ware potatoes. Other crops, such as fruits (e.g., pears, peaches, cherries, blueberries, raspberries, blackberries, and strawberries), may be shipped in containers similarly treated by the method and system disclosed herein. Berries, such as strawberries, are often contaminated with a mold or fungus, which tends to diminish the useful life of such a crop when it reaches an ultimate consumer. Raspberries are particularly vulnerable to mold formation within about 24 hours of being harvested, if allowed to be at room temperature.

Additional or concurrent treatment of containers for berries with an anti-mold, bactericide or fungicide of a volatile nature may increase the useful life of such berries in the hands of an ultimate consumer. The use of 1,4-DMN for crops may achieve such mentioned purposes as well as maintain hydration, which is very important for presentation of plump, healthy-appearing berries on a grocer's shelf.

A "volatile" liquid chemical for the purposes of this invention includes one that has a significant vapor pressure at temperatures as low as 40° F. with a significant increase in vapor pressure with increase in temperature. Liquid chemicals having a volatility similar to that of DMN, especially 1,4-dimethylnaphthalene, are considered to be volatile chemicals for the purposes of this invention.

Given that the purpose of treating a shipping container is to provide an atmosphere of an effective chemical for a particular crop during shipment, an herbicidal, fungicidal, bactericidal chemical that substantially evaporates during shipment (e.g., over a period of several days to a couple of weeks) is sufficiently volatile for the purposes for use in the disclosed methods and systems.

The apparatus and processes described and claimed herein may be used to treat a wide variety of produce during the filling of boxes, cartons, etc., in preparation for shipment to grocers.

The embodiments described herein are not meant to limit the scope of the present invention. In each of the various embodiments, the methods, kits and system described herein disclose a way for collecting a sample and transporting the sample to another location for chemical residue analysis. However, the present invention may be carried out using embodiments different from those specifically described herein. Therefore, the scope of the present invention is not limited by the exemplary embodiments, but is defined by the appended claims.

What is claimed is:

1. An apparatus for applying a predetermined, controlled quantity of a liquid crop-preservative formulation onto a substrate on an interior surface of a container, wherein the liquid crop-preservative formulation comprises a crop-preservative active ingredient and at least one solvent or diluent, the apparatus comprising:
 a reservoir for containing the liquid crop-preservative formulation that comprises the crop-preservative active ingredient and the at least one solvent or diluent;
 a pump for providing a pressurized stream of the liquid crop-preservative formulation;
 transport means to transport the liquid crop-preservative formulation from the reservoir to the pump;
 a sensor configured to sense the container and to send a signal to a controller upon sensing the container under an injection nozzle;

the controller configured to send an actuator signal to a control valve upon receiving the signal from the sensor; and the control valve configured to be opened for a controlled period of time upon receiving the actuator signal from the controller, to cause an injection of a predetermined quantity of the liquid crop-preservative formulation to be injected into the container from the injection nozzle.

2. The apparatus of claim 1, wherein the pump is a mechanical device configured to adjust a quantity of ejectable volatile liquid per unit of time.

3. The apparatus of claim 2, wherein the adjustment means is an electrical device.

4. The apparatus of claim 1, wherein the control valve comprises a solenoid valve.

5. The Apparatus of claim 1, wherein the liquid crop-preservative formulation comprises dimethylnaphthalene (DMN) and at least one solvent.

6. The Apparatus of claim 5, wherein the liquid crop-preservative formulation further comprises at least one of the following: surfactant, aroma enhancer, deodorizer, essential oil, higher alcohol of $C_6$-$C_{12}$ carbon length, bactericide, or fungicide.

* * * * *